United States Patent [19]

Damen et al.

[11] Patent Number: 5,874,595
[45] Date of Patent: Feb. 23, 1999

[54] METHOD FOR THE PREPARATION OF BACCATIN III AND DERIVATIVES THEREOF FROM 10-DEACETYLBACCATIN III

[75] Inventors: Eric Wilhelmus Petrus Damen, Nijmegen; Johan Wilhelm Scheeren, Malden; Dick de Vos, Oegstgeest, all of Netherlands

[73] Assignee: Pharmachemie B.V., Haarlem, Netherlands

[21] Appl. No.: 861,053

[22] Filed: May 21, 1997

[30] Foreign Application Priority Data

May 2, 1997 [EP] European Pat. Off. .............. 97201315

[51] Int. Cl.⁶ .................................................. C07D 305/14
[52] U.S. Cl. ............................................ 549/510; 549/511
[58] Field of Search ...................................... 549/510, 511

[56] References Cited

U.S. PATENT DOCUMENTS 5,629,433  5/1997  Zheng et al. ............................ 549/510

FOREIGN PATENT DOCUMENTS 0336840  10/1989  European Pat. Off. .
0400971  12/1990  European Pat. Off. .
0629701  12/1994  European Pat. Off. .

OTHER PUBLICATIONS

K. Ishihara et al., "Scandium Trifluoromethanesulfonate as an Extremely Active Acylation Catalyst", J. Am. Chem. Soc., vol. 117, No. 15, pp. 4413–4414, 1995.

F. Gueritte–Voegelein et al., "Chemical Studies of 10–Deacetyl Baccatin III. Hemisynthesis of Taxol Derivatives", Tetrahedron, vol. 42, No. 16, pp. 4451–4460, 1986.

Primary Examiner—Ba K. Trinh
Attorney, Agent, or Firm—Browdy and Neimark

[57] ABSTRACT

10-Deacetylbaccatin III is selectively acylated to baccatin III and derivatives thereof in high yield with anhydrides (e.g. acetic anhydride), catalysed by Lewis acids. Extremely effective catalysts in this reaction are compounds of the formula $ML_x$ wherein M is a rare earth metal and L is a anion, preferably a strong electron withdrawing counterion such as triflate.

18 Claims, No Drawings

METHOD FOR THE PREPARATION OF BACCATIN III AND DERIVATIVES THEREOF FROM 10-DEACETYLBACCATIN III

FIELD OF THE INVENTION

This invention relates to the preparation of baccatin III and derivatives thereof from 10-deacetylbacctin III, a very useful precursor in the semisynthesis of the antitumour compound paclitaxel. More precisely, the invention relates to the selective introduction of an acyl group, such as an acetyl group, at the C10-hydroxyl position of 10-deacetylbaccatin III using a Lewis acid catalysed acylation reaction. The resulting baccatin III (if an acetyl group is introduced) or a derivative thereof can be protected or functionalised at the C7-position in high yield and with any desired (protecting)group.

BACKGROUND OF THE INVENTION

The limited availability of the potent antitumour compound paclitaxel (1), isolated from the bark of the Pacific yew tree (Taxus Brevifolia), has motivated scientists to develop an alternative paclitaxel source (Farina (ed.), *The Chemistry and pharmacology of Taxol® and its derivatives*, Elsevier Science Amsterdam, 1995, p 7–53). An attractive alternative is the semisynthesis from a paclitaxel precursor isolated from a renewable source. Though many precursors have been isolated and converted into paclitaxel and analogues, these semisyntheses are either too complex, (for example taxine B (Wiegerinck et al., *J. Org. Chem.*, 1996, 61, 7092)), or the amount of isolated precursor is too low (like baccatin III (2) (Halsall et al., *J. Chem. Soc., Chem. Commun.*, 1970, 216)) to be economically feasible. A useful precursor was discovered by Potier et al (*C. R. Acad. Sc.*, 1981, 293, série II, 501), who isolated 10-deacetylbaccatin III (3) from the leaves of the European yew (Taxus Baccata). Meanwhile it has been demonstrated that this precursor can be isolated relatively easy and in significant amounts (Pilard et al., PCT Application, WO 94/07882).

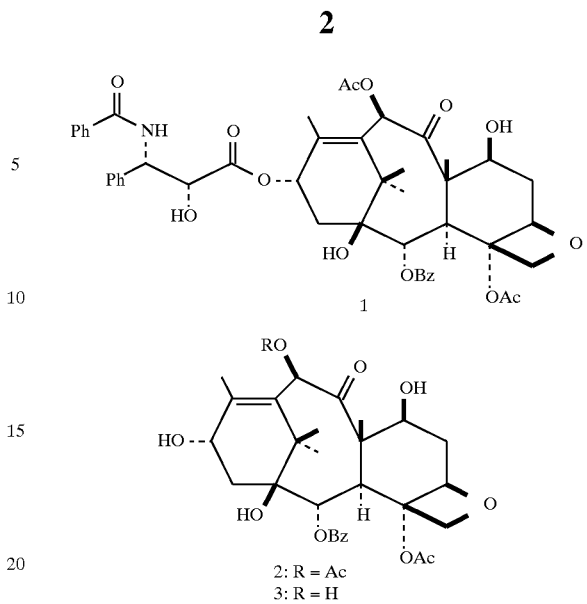

2: R = Ac
3: R = H

In the first reported semisynthesis by Greene et al (*J. Am. Chem. Soc.*, 1988, 110, 5917), 10-deacetylbaccatin III is converted into paclitaxel in four steps (scheme 1). Under what are claimed to be carefully optmised conditions, 10-deacetylbaccatin III (3) is protected at the C7-position using 20 equivalents of triethylsilyl chloride in pyridin at 0° C. (c.y. 78%). Acylation with 10 equivalents of acetylchloride for 48 hours at 0° C. results in 7-triethylsilyl-baccatin III in 86% yield. Treatment with excess protected side chain in the presence of di-2-pyridyl carbonate (DPC) and 4 thylamino pyridine (DMAP) at 73° C. for 100 hours gave protected paclitaxel in 80% yield at 50% conversion. Deprotection of the C7- and C2'-position in 89% yield gave paclitaxel (1) in an overall yield of 24% starting from 10-deacetylbaccatin III (3) (48% when based on 50% conversion in step three).

Scheme 1

(a) TES-Cl/pyridin; 78%.
(b) AcCl/pyridin; 86%.
(c) DPC/DMAP/73° C.; 80% (at 50% conversion).
(d) 0.5% HCl/EtOH/0° C.

The attachment of the side chain, the weakest point in the synthesis described above, has been improved through the years. For example, Holton et al. developed a process involving the use of β-lactam (4) to couple to 7-triethylsilylbaccatin III in 92% yield to obtain paclitaxel in an overall yield of 61% from 10-deacetylbaccatin III (Holton et al., Eur. Patent Application, 0,400,971). A second improved introduction of the side chain in 100% yield at 77% conversion involves an oxazinone (5). The overall yield from 10-deacetylbaccatin III is 66% (Holton et al., Eur. Patent Application 0,428,376). A third example of a high-yield side chain attachment to 7-triethylsilylbaccatin III uses oxazolidine (6) (94% yield), resulting in an overall yield of 64% (Greene et al., *J. Chem. Soc., Chem. Commun.*, 1994, 2591).

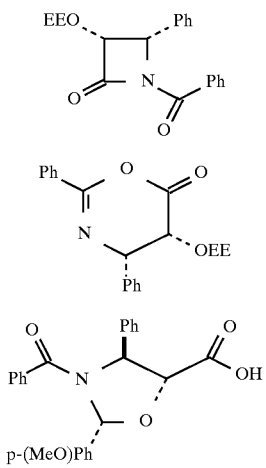

The examples above illustrate that the weak point in the paclitaxel semisynthesis is no longer the attachment of the protected side chain but the conversion of 10-deacetylbaccatin III into C7-O-protected baccatin III.

OBJECT OF THE INVENTION

The object of this invention is to provide a method for an efficient single step conversion of 10-deacetylbaccatin III into baccatin III, which is a superior starting material for an improved semisynthesis of paclitaxel or paclitaxel analogues.

Another object of this invention is the provision of a method for an efficient conversion of 10-deacetylbaccatin III into baccatin III derivatives.

DETAILED DESCRIPTION OF THE INVENTION

This invention relates to a new strategy in the semisynthesis of paclitaxel by selective acetylation of 10-deacetylbaccatin III to baccatin III. Classic acetylation methods with acetic anhydride and pyridine, for example, result in a mixture of baccatin III and 7-acetyl-10-deacetylbaccatin III in the ratio of approximately 1:1 (Potier et al., *Tetrahedron*, 1986, 42, 4460) or acetylation occurs selectively at the C7-hydroxyl (Kingston et al.,*J. Or. Chem.*, 1986, 51, 3239). Various Lewis acids are known to catalyse the acylation of alcohols with acid anhydrides (Yamamoto et al.,*J. Am. Chem. Soc.*, 1995, 117, 4413 and references cited therein). We have investigated whether Lewis acids could influence selectivety in the acetylation of the secondary OH-functions of 10-deacetylbaccatin III. We found that the use of Lewis acids in the reaction of 10-deacetylbaccatin III with acetic anhydride caused selective acetylation of the C10-hydroxyl group. This method can also be applied for improving the acetylation of 7-protected-10-deacetylbaccatin III (scheme 2).

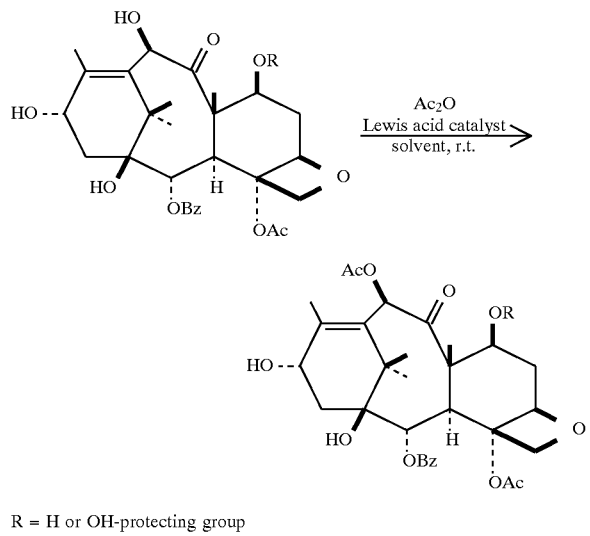

R = H or OH-protecting group

It must be recognised that acetylation is also possible with other acetyl donors, for example a mixed anhydride of p-nitrobenzoic acid and acetic acid or acetyl chloride. The method is generally applicable to the acylation with anhydrides or mixed anhydrides of any carboxylic acid or acyl halides to prepare any C10-O-acyl derivatives of 10-deacetylbaccatin III.

Extremely effective catalysts in this reaction are the rare earth metal Lewis acid catalysts $ML_x$, where M=La, Ce, Pr, Nd, Pm, Sm, Eu, Gd, Tb, Dy, Ho, Tb, Er, Tm, Yb or Lu and L=any counter ion, preferably a strong electron withdrawing counter ion like $OTf^-$, $ClO_4$- or NTf2-, which leads to stronger Lewis acidity. The obtained yields are excellent and the reaction is completed within a few hours at room temperature. No large excess of acylating reagent is necessary and after an easy workup the product is sufficiently pure to proceed with in the next reaction steps. The rare earth metal salts themselves are cheap, non-toxic materials that can be recovered and reused after the reaction. Lewis acids like $TiCl_4$, $ZnCl_2$, $Sc(OTf)_3$, $AlCl_3$ are also able to convert 10-deacetylbacctin III selectively into baccatin III; compared to rare earth metal catalysts, the reaction proceeds more slowly, with lower conversion and usually 10 mol % of catalyst is required. With respect to the use of solvents, conversion rates seem to depend on the solubility of 10-deacetylbaccatin III (see table 1, example 3). The method described above allows us to use baccatin III as a key reagent in the synthesis of paclitaxel by protecting the C7-hydroxyl with any protecting group, followed by attachment of the side chain and deprotection. By this method, paclitaxel can be prepared more easily, with simpler reagents, in shorter reaction times, with less purification steps and in higher yields than the method described by Greene et al. (Eur. Patent Application 0,336,840).

Furthermore, it is possible to introduce a (protected) water soluble group or any other enzymatically cleavable group at the C-7 hydroxyl of baccatin III. After coupling of the side chain and deprotection this results in a semi-synthetic paclitaxel prodrug. By this method it is also possible to easily prepare C10-O-acyl paclitaxel derivatives, which are known to have the same biological activity as paclitaxel (Rao et al., J.Med.Chem 1995, 38, 3411).

Example 1

Preparation of baccatin III (2) using 1 mol % of ytterbium trifluoromethanesulfonate To a stirred solution of 300 ng (0.553 mmol) of 10-deacetylbaccatin III (3) in 20 mL of freshly distilled tetrahydrofuran 78 μL (1.5 eq.) of acetic anhydride was added, followed by 50 μL of a solution of 35 mg of commercial ytterbium trifluoromethanesulfonate hydrate in 2.0 mL of tetrahydrofuran. After two hours no starting material could be detected by means of TLC (Silica 60, $CH_2Cl_2$/MeOH 9:1). The reaction mixture was diluted with 20 mL of ethylacetate and 20 mL of a saturated aqueous sodium hydrogencarbonate solution. The aqueous layer was extracted three times with 15 mL portions of ethylacetate. The combined organic layers were washed with brine, dried over anhydrous sodiumsulfate, filtered and concentrated in vacuo to afford the crude product, which was >95% pure. Further purification was done by flash column chromatography (Silica 60H, $CH_2Cl_2$/MeOH 99:1) to yield 310 mg of baccatin III (2) (96%), m.p. 243°–245° C. (lit: 236°–238° C.). $C_{31}H_{38}O_{11}$ calculated C 63.47% H 6.53% measured C 63.16% H 6.62%. FAB-MS m/z 587 [M+H]$^+$, 609 [M+Na]$^+$. $^1$H-NMR (300 MHz, CDCl$_3$) δ (ppm)=1.07 (s, 3H), 1.07 (s, 3H), 1.65 (s, 3H), 1.94 (s, 3H), 2.17 (s, 3H), 2.21 (s, 3H), 2.30 (m, 3H), 2.58 (m, 1H), 3.87 (d, 1H, J=7.0), 4.15 (d, 1H, J=8.3), 4.28 (d, 1H, J=8.3), 4.46 (dd, 1H, J=6.7, 10.8), 4.87 (t, 1H, J=7.7), 4.97 (d, 1H, J=7.8), 5.60 (d, 1H, J=7.0), 6.31 (s, 1H), 7.47 (t, 2H, J=7.6), 7.59 (t, 1H, J=7.6), 8.09 (d, 2H, J=7.6).

Example 2

Preparation of baccatin III (2) using 10 mol % of scandium trifluoromethanesulfonate To a solution of 50 mg (91.9 μmol) of 10-deacetylbaccatin III and 13 μL (1.5 eq.) of acetic anhydride in 2.0 mL of freshly distilled tetrahydrofuran 100 μL of a solution of 4.5 mg of commercial scandium trifluoromethanesulfonate in 1.0 mL of tetrahydrofuran was added. The reaction mixture was stirred at room temperature for 48 hours. Usual workup and isolation of the product by means of preparative TLC (Silica 60, CH2Cl2/MeOH 10:1) afforded 9 mg of unreacted 10-deacetylbaccatin III (18%) along with 31 mg of baccatin III (58%). 1H-NMR and Rf-value (TLC) were in accordance with the product from example 1.

Example 3

Preparation of Baccatin III with Various Lewis Acid Catalysts

To a solution of 50 mg (91.9 μmol) of 10-deacetylbaccatin III and 13 μL (1.5 eq.) of acetic anhydride in 2.0 mL of solvent 10–100 μL of a solution of 1.0 eq. of catalyst in 1.0 mL of the solvent was added. An overview of the various catalysts, the amount of catalyst, the solvents, the reaction times and the results are presented in table 1.

TABLE 1

Lewis acid catalysed acetylation of 10-deacetylbaccatin III

| catalyst | mol % | solvent | reaction time | yield % |
|---|---|---|---|---|
| TiCl$_4$ | 10 | THF | 48 hours | 20[a] |
| ZnCl$_2$ | 10 | THF | 48 hours | 50[b] |
| AlCl$_3$ | 10 | THF | 48 hours | 60[a] |
| CeCl$_3$ | 1 | THF | 24 hours | >95[b] |
| Yb(OTf)$_3$ | 1 | CH$_2$Cl$_2$ | 24 hours | >95[b] |
| Yb(OTf)$_3$ | 1 | EtOAc | 3 hours | >95[a] |
| Yb(NO$_3$)$_3$ | 1 | CH$_2$Cl$_2$ | 24 hours | >95[b] |
| La(OTf)$_3$ | 1 | THF | 2 hours | 97[c] |
| Lu(OTf)$_3$ | 1 | THF | 3 hours | 80[a] | a) along with unreacted 10-deacetylbaccatin III, according to TLC. b) according to 300 MHz $^1$H-NMR. c) isolated yield.

Example 4

Preparation of 7-(2,2,2-trichloroethoxycarbonyl)-baccatin III

Baccatin III used in this example (prepared as described in example 1) was used without chromatographic purification. A solution of 103 mg (0.176 mmol) of baccatin III (2), 50 μL of pyridine and 2.8 mg of 4-(dimethylamino)pyridine in 2.0 mL of dichloromethane was stirred at room temperature under an argon atmosphere. To the mixture 50 μL (2.0 eq) of 2,2,2-trichloroethyl chloroformate was added. After 45 minutes an additional 30 μL of 2,2,2-trichloroethyl chloroformate was added and stirring was continued for another 10 minutes. TLC (Silica 60, $CH_2Cl_2$/MeOH 9:1) showed that no starting material was present in the reaction mixture. The reaction mixture was diluted with 30 mL of dichloromethane and successively washed with 15 mL portions of aqueous 0.5N potassium bisulfate, demineralised water, aqueous saturated sodium bicarbonate and brine. The organic layer was dried over anhydrous sodium sulfate and evaporated. The resulting white residue was sonicated in diethylether and filtrated. Recrystallisation in methanol afforded 7-(2,2,2-trichloroethoxycarbonyl)-baccatin III, yield 129 mg (96%) M.p. 208°–211° C. $C_{34}H_{39}Cl_3O_{13}$ calculated C 53.59% H 5.16% measured C 53.79% H 5.00%. FAB-MS m/z 785 [M+Na]$^+$, $^1$H-NMR (300 MHz, CDCl$_3$) δ (ppm)=1.08 (s, 3H), 1.12 (s, 3H), 1.82 (s, 3H), 2.00 (m, 1H), 2.11 (s, 3H), 2.15 (s, 3H), 2.29 (s, 3H), 2.30 (m, 2H), 2.60 (m, 1H), 4.01 (d, 1H, J=7.0), 4.15 (d, 1H, J=8.5), 4.32 (d, 1H, J=8.5), 4.64 (d, 1H, J=12.0), 4.81 (t, 1H, J=7.0), 4.98 (d, 1H, J=8.0), 5.03 (d, 1H, J=12.0), 5.62 (dd, 1H, J=7.0, 11.0), 5.63 (d, 1H, J=7.0), 6.39 (s, 1H), 7.48 (t, 2H, J=7.6), 7.61 (t, 1H, J=7.5), 8.10 (d, 2H, J=7.6).

Example 5

Preparation of 10-benzoyl-10-deacetylbaccatin III

To a solution of 50 mg (91.9 μmol) of 10-deacetylbaccatin III and 13 μL (1.5 eq.) of benzoic anhydride in 2.0 mL of freshly distilled tetrahydrofuran 100 μL of a solution of 5.8 mg of commercial ytterbium trifluoromethanesulfonate hydrate in 1.0 mL of tetrahydrofuran was added. The reaction mixture was stirred at room temperature for 48 hours. Usual workup and isolation of the product by means of preparative TLC (Silica 60, CH2Cl2/MeOH 10:1) afforded 11 mg unreacted 10-deacetylbaccatin III (22%) along with 29 mg of 10-benzoyl-10deacetylbaccatin III (62%), m.p. 154°–156° C. $C_{36}H_{40}O_{11}$ calculated C 66.66% H 6.22% measured C 66.50% H 6.23%. $^1$H-NMR (300 MHz, CDCl$_3$) δ (ppm)=1.18 (s, 3H), 1.25 (s, 3H), 1.69 (s, 3H), 1.80–1.93 (m, 1H), 2.09 (s, 3H), 2.16–2.23 (m, 2H), 2.29 (s, 3H), 2.53–2.61 (m, 1H), 3.95 (d, 1H, J=6.9), 4.17 (d, 1H, J=8.3), 4.32 (d, 1H, J=8.3), 4.55 (dd, 1H, J=6.6, 10.6), 4.91 (br t, 1H, J=7.9), 5.00 (d, 1H, J=9.2), 5.67 (d, 1H, J=6.9), 6.59 (s, 1H), 7.40–7.52 (m, 4H), 7.54–7.61 (m, 2H), 8.04–8.14 (m, 4H).

Example 6

Preparation of 7-triethylsilylbaccatin III via baccatin III

A solution of 50 mg (85.3 μml) of baccatin III and 59.5 μL (5.0 eq.) of triethylamine in 2.0 mL of dichloromethane was stirred at 0° C. under an argon atmosphere. To the mixture 71.6 μL (5.0 eq) of chlorotriethylsilane was added and the ice bath was removed. When no more starting material could be detected by means of TLC (Silica 60, CH2Cl2/MeOH 10:1) the reaction mixture was diluted with 20 mL of dichloromethane and successively washed with 15 mL portions of aqueous 0.5N potassium bisulfate, demineralised water, aqueous saturated sodium bicarbonate and brine. The organic layer was dried over anhydrous sodium sulfate and evaporated. Isolation of the product by means of preparative TLC (Silica 60, CH2Cl2/MeOH 10:1) yields 47 mg (79%) of the title compound. M.p. 252°–254° C. [a]$_D^{23}$=84.1° (c=0.36; methanol) (lit.: 48.6°). $^1$H-NMR (300 MHz, CDCl$_3$) δ (ppm)=0.53–0.59 (m, 6H), 0.92 (t, 9H, J=7.8), 1.03 (s, 3H), 1.19 (s, 3H), 1.68 (s, 3H), 1.83–1.92 (m, 1H), 2.14 (s, 3H), 2.17 (s, 3H), 2.22–2.31 (m, 2H), 2.26 (s, 3H), 2.47–2.58 (m, 1H), 3.80 (d, 1H, J=7.0), 4.14 (d, 1H, J=8.3), 4.30 (d, 1H, J=8.3), 4.48 (dd, 1H, J=6.6, 10.4), 4.84 (br t, 1H, J=8.0), 4.97 (d, 1H, J=8.1), 5.63 (d, 1H, J=7.1), 6.42 (s, 1H), 7.45–7.50 (m, 2H), 7.58–7.60 (m, 1H), 8.09–8.12 (m, 2H).

We claim:

1. A method for preparing baccatin III directed from 10-deacetylbaccatin III comprising:
   acetylating 10-deacetylbaccatin III with acetic anhydride, a mixed anhydride of acetic acid and any other carboxylic acid or an acetyl halide, and a Lewis acid catalyst.

2. A method according to claim 1 wherein the Lewis acid catalyst is a compound comprising a rare earth metal and a counter ion, wherein the rare earth metal is selected from the group consisting of La, Ce, Pr, Nd, Pm, Sm, Eu, Gd, Tb, Dy, Ho, Er, Tm, Yb and Lu.

3. A method according to claim 2, characterized in that the counter ion is a strong electron withdrawing counter ion.

4. A method according to claim 3, wherein the counter ion is triflate (trifluoromethanesulfonate).

5. A method for the preparation of 7,10-difunctionalized 10-deacetylbaccatin III of the general formula

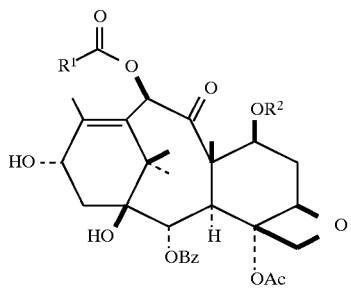

wherein R$^1$ is an alkyl or aryl group and R$^2$ is an OH-protecting group, a (protected) water soluble group or a (protected) prodrug moiety, comprising using the method of claim 1.

6. A method for the preparation of paclitaxel (taxol) via baccatin III, characterized in that the method according to claim 1 is employed.

7. A method for the preparation of paclitaxel (taxol) via baccatin III, characterized in that the method according to claim 2 is employed.

8. A method for the preparation of paclitaxel (taxol) via baccatin III, characterized in that the method according to claim 3 is employed.

9. A method for acetylating 10-deacetylbaccatin III derivatives of the general formula

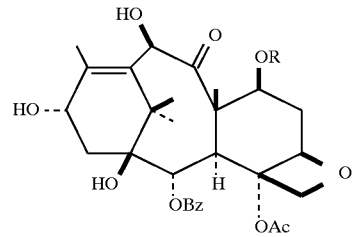

wherein R is a lower alkylsilyl group, characterized by employing the acetylating method of claim 2.

10. A method for acetylating 10-deacetylbaccatin III derivatives of the general formula

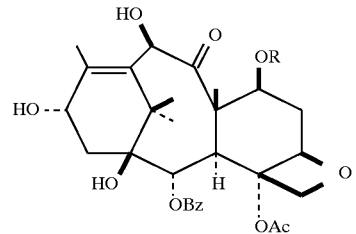

wherein R is a lower alkylsilyl group, characterized by employing the acetylating method of claim 3.

11. A method for acetylating 10-deacetylbaccatin III derivatives of the general formula

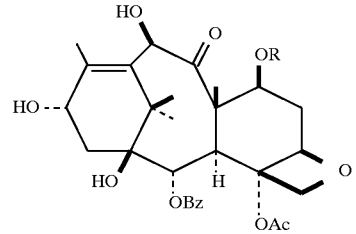

wherein R is a lower alkylsilyl group, characterized by employing the acetylating method of claim 4.

12. A method for the preparation of 7, 10-difunctionalized 10-deacetyl-baccatin III of the general formula

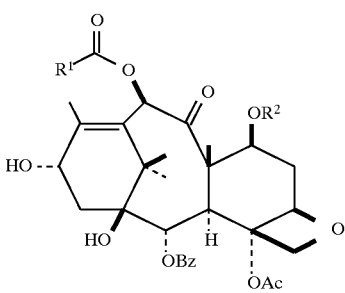

wherein R$^1$ is an alkyl or aryl group and R$^2$ is an OH-protecting group, a (protected) water soluble group or a (protected) prodrug moiety, comprising using the method of claim 2.

13. A method for the preparation of 7, 10-difunctionalized 10-deacetyl-baccatin III of the general formula

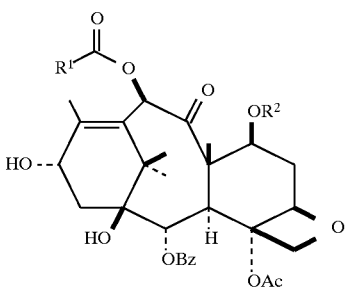

wherein R$^1$ is an alkyl or aryl group and R$^2$ is an OH-protecting group, a (protected) water soluble group or a (protected) prodrug moiety, comprising using the method of claim 2.

14. A method for the preparation of 7, 10-difunctionalized 10-deacetyl-baccatin III of the general formula

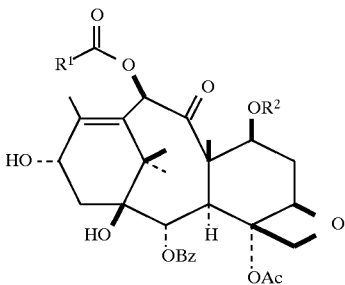

wherein R$^1$ is an alkyl or aryl group and R$^2$ is an OH-protecting group, a (protected) water soluble group or a (protected) prodrug moiety, comprising using the method of claim 3.

15. A method for the preparation of 7, 10-difunctionalized 10-deacetyl-baccatin III of the general formula

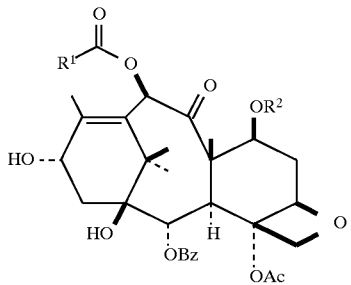

wherein R$^1$ is an alkyl or aryl group and R$^2$ is an OH-protecting group, a (protected) water soluble group or a (protected) prodrug moiety, comprising using the method of claim 4.

16. A method for preparing paclitaxel using baccatin III wherein the baccatin III is prepared according to the method of claim 4.

17. A method for selective C10-O-acylation of 10-deacetylbaccatin III to introduce an acyl group having at least three carbon atoms, comprising acylating 10-deacetylbaccatin III using an anhydride, a mixed anhydride or an acyl halide, wherein the acylation reaction is catalyzed by a Lewis acid.

18. A method for acetylating 10-deacetylbaccatin III derivatives of the formula:

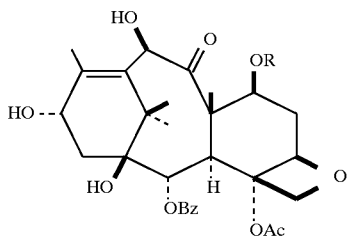

wherein R is a lower alkyl silyl group, comprising acetylating the 10-deacetylbaccatin III in a method according to claim 1.

* * * * *